(12) United States Patent
Inaba et al.

(10) Patent No.: US 8,262,888 B2
(45) Date of Patent: Sep. 11, 2012

(54) CAPILLARY ELECTROPHORESIS APPARATUS

(75) Inventors: Ryoji Inaba, Hitachinaka (JP);
Motohiro Yamazaki, Mito (JP);
Tomohiro Shoji, Hitachinaka (JP);
Takeshi Ohura, Hitachinaka (JP);
Takashi Gomi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 558 days.

(21) Appl. No.: 12/073,296

(22) Filed: Mar. 4, 2008

(65) Prior Publication Data

US 2008/0217177 A1 Sep. 11, 2008

(30) Foreign Application Priority Data

Mar. 5, 2007 (JP) ................... 2007-053660

(51) Int. Cl.
*G01N 27/447* (2006.01)
*G01N 27/453* (2006.01)
(52) U.S. Cl. .................. 204/603; 356/344; 356/410
(58) Field of Classification Search .................. 204/452, 204/603; 356/344, 410, 411, 440
See application file for complete search history.

(56) References Cited

U.S. PATENT DOCUMENTS

| | | | | |
|---|---|---|---|---|
| 5,516,409 A | * | 5/1996 | Kambara | 204/603 |
| 5,833,827 A | * | 11/1998 | Anazawa et al. | 204/603 |
| 6,017,765 A | * | 1/2000 | Yamada et al. | 623/1.15 |
| 2005/0211558 A1 | * | 9/2005 | Sonehara et al. | 204/601 |

FOREIGN PATENT DOCUMENTS

JP 2004-144479 5/2004

* cited by examiner

*Primary Examiner* — J. Christopher Ball
(74) *Attorney, Agent, or Firm* — McDermott Will & Emery LLP

(57) ABSTRACT

There is provided a capillary electrophoresis apparatus wherein coupling efficiency of exciting irradiation light to a capillary array does not decline even if any one capillary array of two capillary arrays is removed.
Light emission generated by capillaries of each capillary array of $2^n$ (n is a positive integer) capillary arrays radiating exciting light from one side is detected by one optical detection system.

9 Claims, 11 Drawing Sheets

FIG. 1
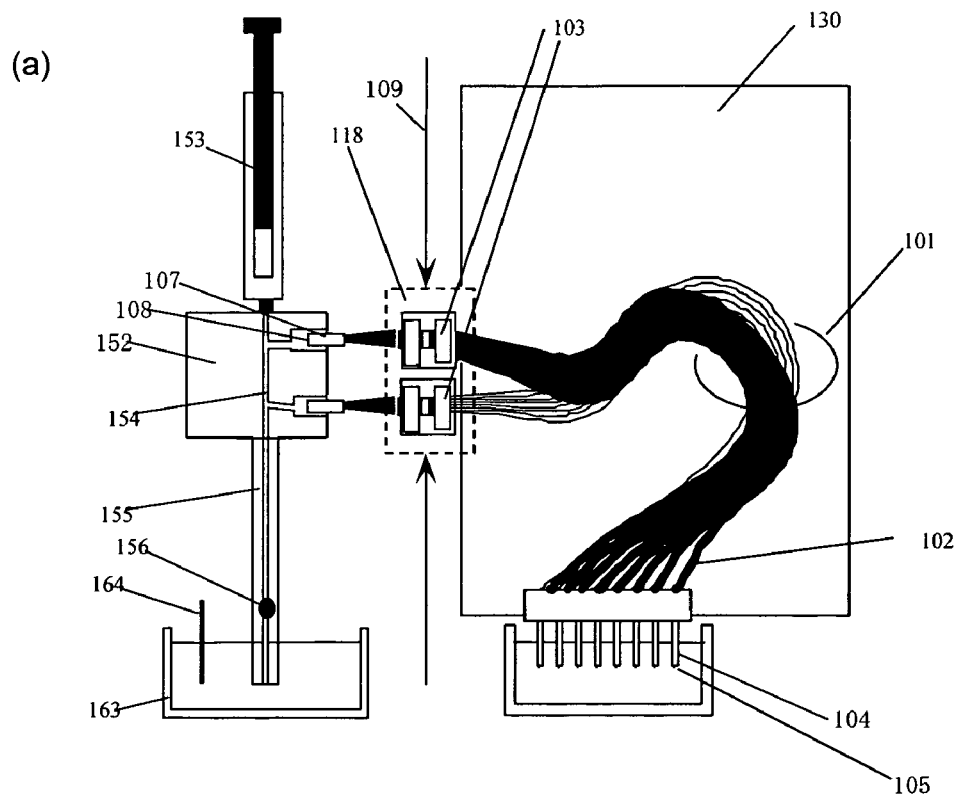
(a)
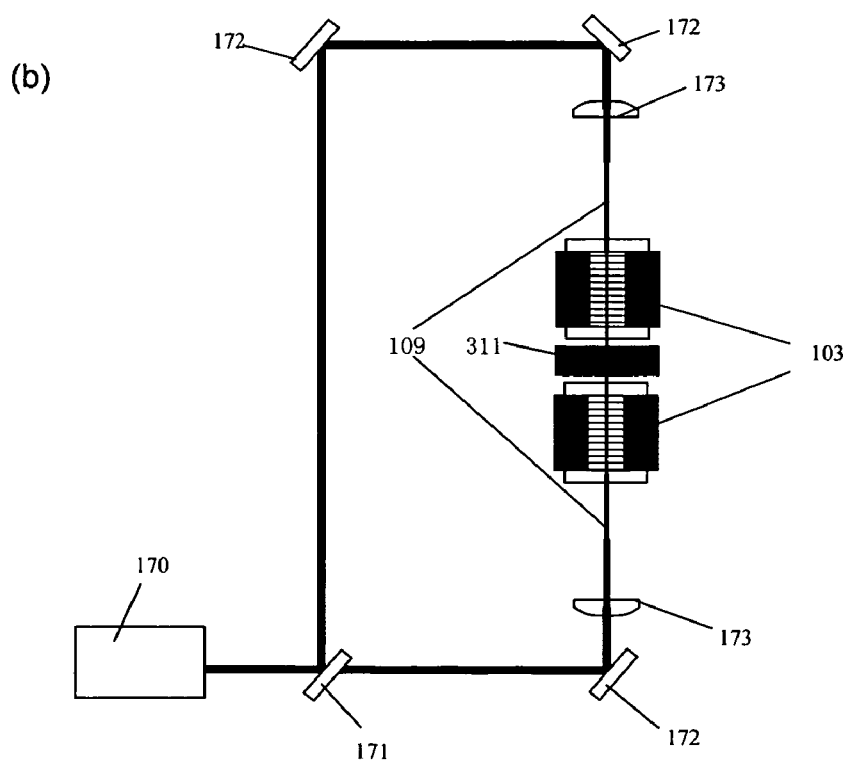
(b)

FIG. 2
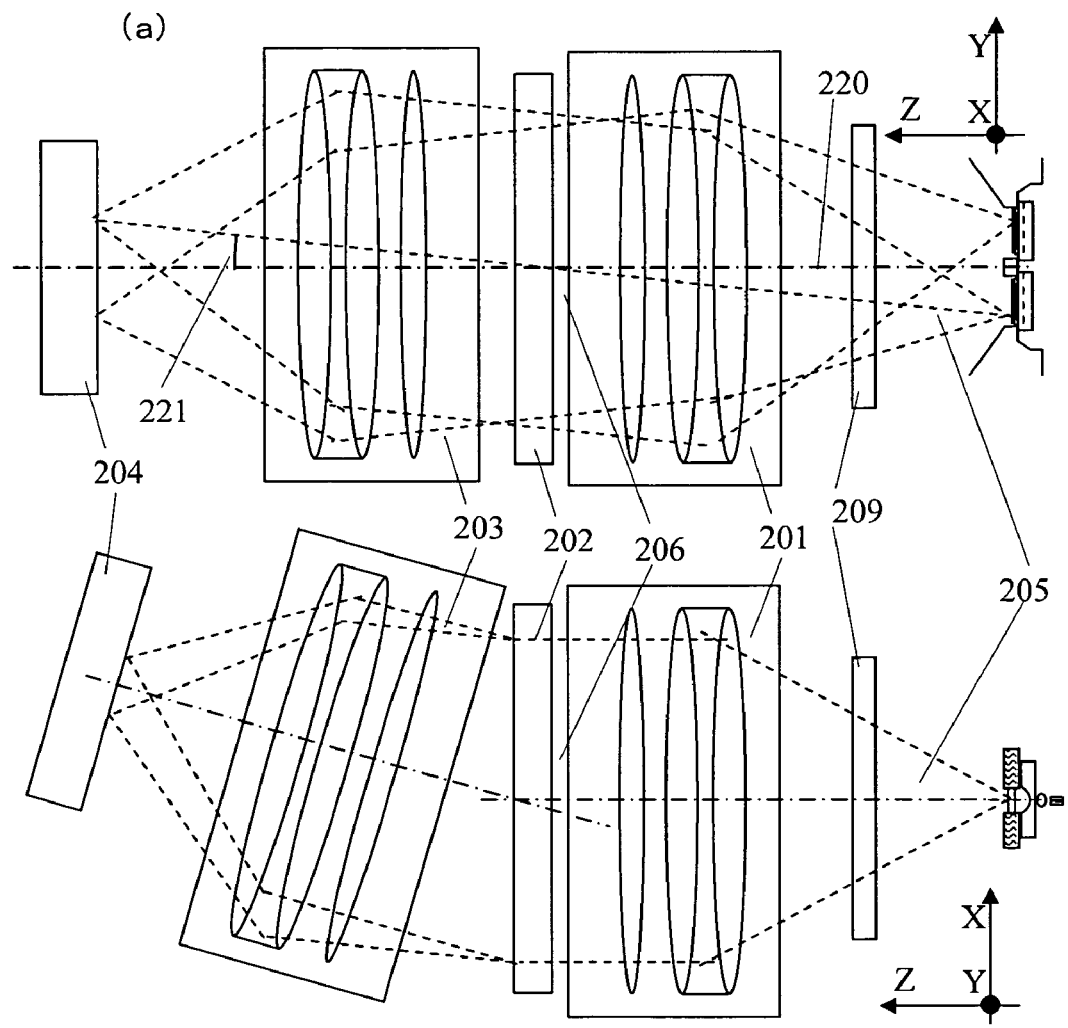
(a)
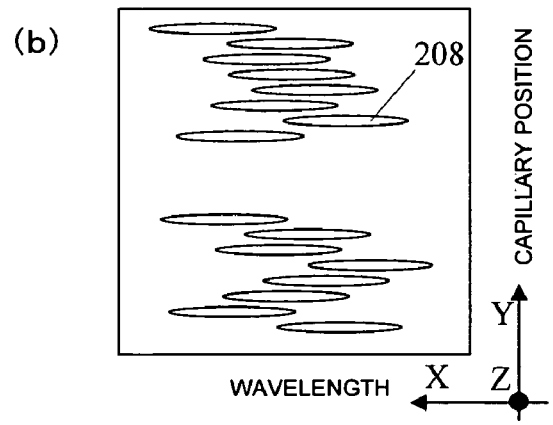
(b)

FIG. 5
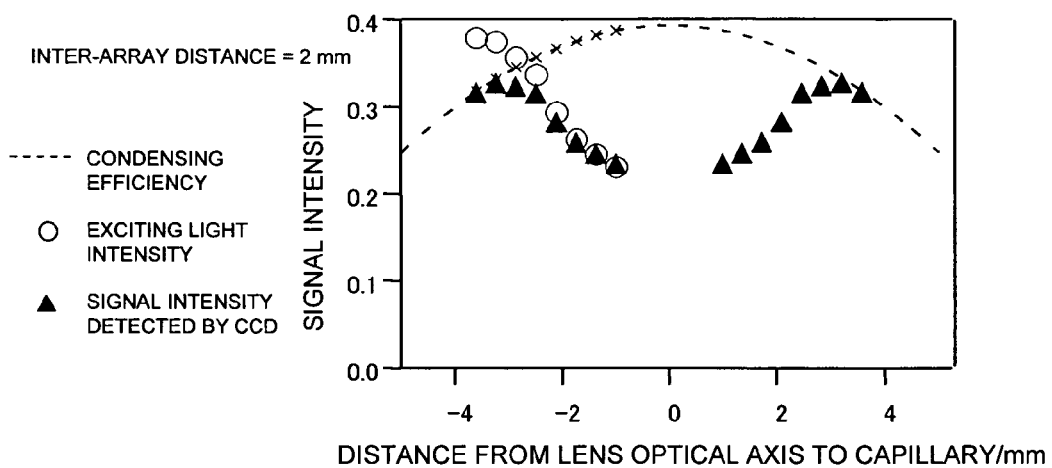
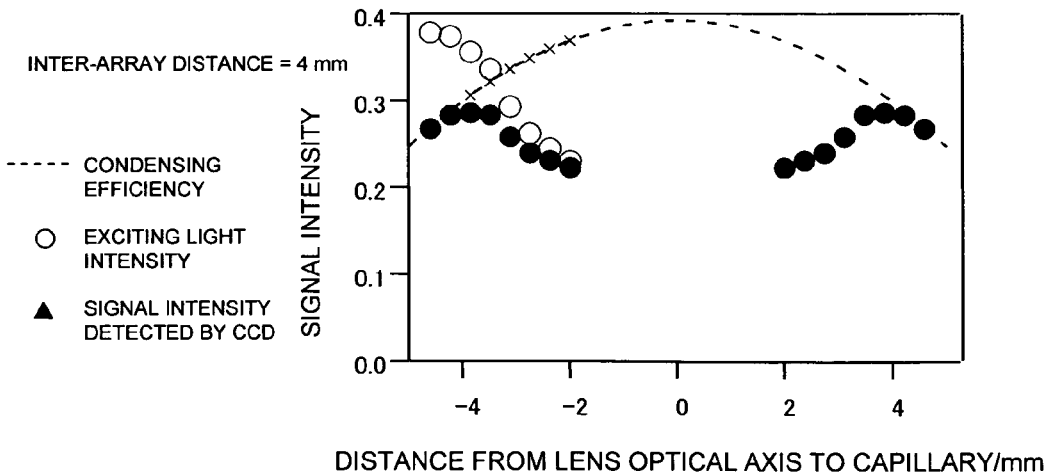

⊗ AVERAGE VALUE OF SIGNAL INTENSITY OF 16 CAPILLARIES DETECTED BY CCD (IN BROKEN LINE IS AVERAGE VALUE OF EXCITING LIGHT INTENSITY IN EIGHT CAPILLARIES)

✶ STANDARD DEVIATION/AVERAGE VALUE OF SIGNAL INTENSITY OF 16 CAPILLARIES DETECTED BY CCD (IN BROKEN LINE IS STANDARD DEVIATION/AVERAGE VALUE OF EXCITING LIGHT INTENSITY IN EIGHT CAPILLARIES)

FIG. 7

| METHOD | 2-ARRAY DOUBLE-SIDED THROUGH IRRADIATION | 2-ARRAY SINGLE-SIDED IRRADIATION | 2-ARRAY DOUBLE-SIDED IRRADIATION WITH OPTICAL STOPPER (PRESENT INVENTION) |
|---|---|---|---|
| a SIGNAL INTENSITY | ◎ | ○ | ○ |
| b SIGNAL INTENSITY DISPERSION FOR TWO ARRAYS | ◎ | ✕            ◎ | ◎ |
| c SIGNAL-TO-NOISE RATIO FOR ONE ARRAY | ✕ | ◎ | ◎ |
| d FALSE PEAK | ○ | ◎ | ◎ |
| e RETURNED LIGHT | ○ | ◎ | ◎ |
| f NUMBER OF FLUORESCENCE CONDENSING SYSTEMS | ◎ (1) | ✕ (2) PRACTICALLY IMPOSSIBLE WITH SINGLE DETECTION SYSTEM DUE TO MUTUAL INTERFERENCE | ◎ (1) |

FIG. 9
(a)
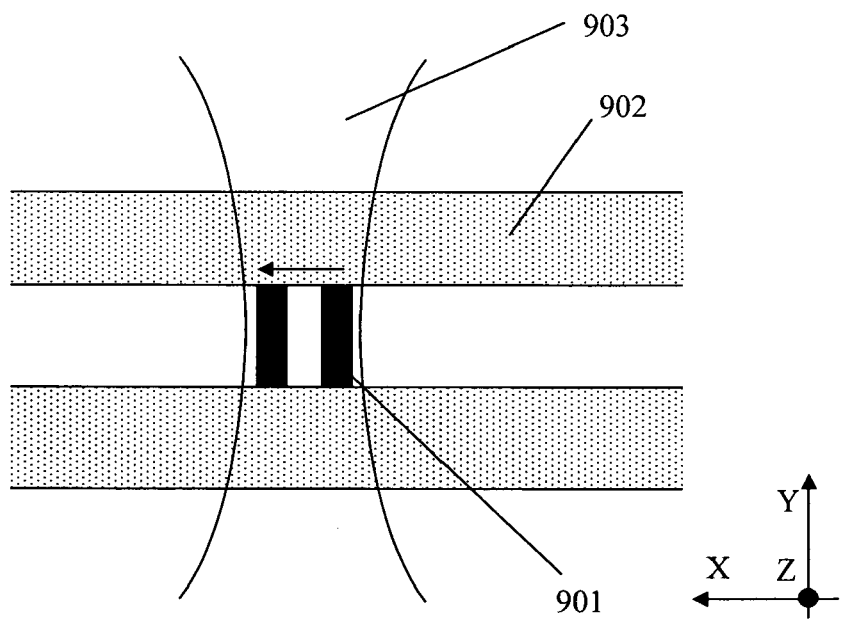
(b)
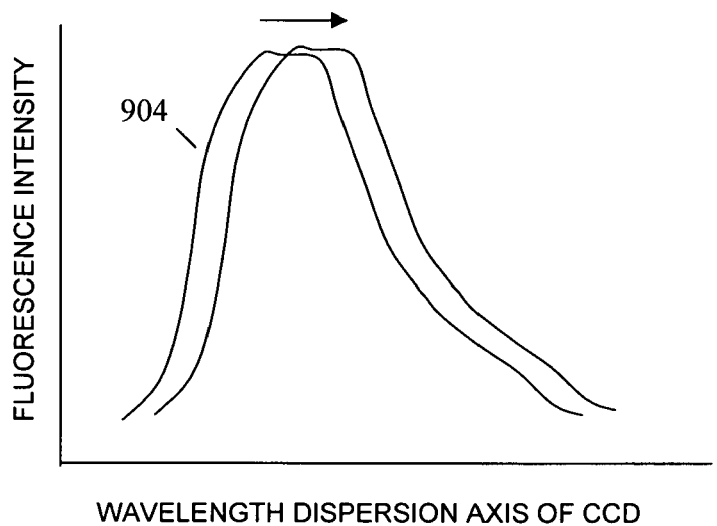
WAVELENGTH DISPERSION AXIS OF CCD

CAPILLARY ELECTROPHORESIS APPARATUS

BACKGROUND OF THE INVENTION

1. Field of the Invention

The present invention relates to a technology to separate and analyze nucleic acids, proteins and the like by means of electrophoresis and, for example, relates to a capillary electrophoresis apparatus.

2. Description of the Related Art

Japanese Patent Application Laid-Open No. 2004-144479 discloses a capillary electrophoresis apparatus. The capillary electrophoresis apparatus uses an electrophoresis method using a capillary made of a silica tube and a polymer coating that coats the silica tube for the purpose of determining a base sequence and base length of DNA. A voltage is applied to both ends of the capillary after a sample containing DNA to be measured being injected into a separation medium such as polyacrylamide in the silica capillary. A DNA compound in the sample migrates inside the capillary to generate DNA bands in the capillary after being separated based on molecular weight or the like. Each DNA band has added fluorochrome and thus, develops colors after being irradiated with laser light. By reading such colors using a fluorometric means, the DNA sequence is determined. Constitution of proteins can also be examined by performing separation/analysis of proteins in the same manner.

A method of light irradiation to a sample in the capillary electrophoresis apparatus disclosed in Japanese Patent Application Laid-Open No. 2004-144479 is as follows. That is, a capillary at one end of a capillary array consisting of a plurality of capillaries arranged on a plane substrate or capillaries at both ends of the capillary array are irradiated with a laser light and the laser light crosses the capillary array by propagating successively from one capillary to the adjacent one. A fluorescence detection method is as follows. That is, an image in a laser irradiation part on the capillary array is formed on a secondary CCD through a condensing lens, a transmission grating, and an image formation lens.

If, in a system in which a capillary at one end of a capillary array consisting of a plurality of capillaries arranged on a plane substrate or capillaries at both ends of the capillary array are irradiated with a laser light and the laser light crosses the capillary array by propagating successively from one capillary to the adjacent one, the focal point of the laser light is adjusted on capillaries at both ends, the laser light can efficiently be coupled to the capillary array. Moreover, in a process in which the laser light propagates through a plurality of capillaries, a reflection loss of the laser light is produced on the outside diameter of the capillary based on a difference of the index of refraction between quartz and air. Therefore, if the laser light is radiated from one side, irradiation light intensity will not be uniform among the plurality of capillaries. To minimize intensity variations in the capillary array, the laser light is generally radiated from both sides of the capillary array. Moreover, since a separation medium is present in the capillary tube, the inside diameter and outside diameter of the capillary and the like are determined in such a way that efficiency with which the laser light propagates from capillary to capillary is maximized by adjusting to the index of refraction of the separation medium.

The above conventional capillary electrophoresis apparatus has, as described below, a problem that gel, which is a separation medium, is consumed wastefully. Assume, for example, that six samples are measured in a capillary electrophoresis apparatus having 16 capillaries. If the capillary is filled with air, the efficiency with which exciting irradiation light propagates from capillary to capillary declines compared with a case in which the capillary tube is filled with a separation medium because the index of refraction in the capillary tube becomes smaller. Thus, a problem of rising running costs exists because the separation medium must be injected into all 16 capillaries even though the number of samples is six.

If capillaries consist of two independently removable capillary arrays, each of which having eight capillaries, and six samples are measured, the above problem of wastefully consuming the separation medium can be solved by means of a system that allows removal of one capillary array when six samples are measured. In this case, however, another problem arises. If both capillary arrays are radiated from one side, signal intensity variations increase among capillaries. If two capillary arrays are irradiated with exciting irradiation light on both sides and one of the capillary arrays is removed, a problem arises that coupling efficiency of exciting irradiation light to the capillary arrays declines because no capillary will be present at a focal point of light.

The present invention has been developed in view of the above situation and an object thereof is to provide a capillary electrophoresis apparatus capable of mounting $2^n$ (n is a positive integer) capillary arrays, wherein coupling efficiency of exciting irradiation light to the capillary arrays does not decline even if any one capillary array is removed.

SUMMARY OF THE INVENTION

A capillary electrophoresis apparatus according to the present invention detects emission of light emitted from capillaries of each capillary array of $2^n$ (n is a positive integer) capillary arrays irradiated with exciting light from one side by one optical detection system.

According to the present invention, a capillary electrophoresis apparatus to which $2^n$ (n is a positive integer) capillary arrays can be attached, wherein coupling efficiency of exciting irradiation light to the capillary arrays does not decline even if any one capillary array is removed is realized.

BRIEF DESCRIPTION OF THE DRAWINGS

FIG. 1A is a schematic diagram of a capillary electrophoresis apparatus of the present invention and FIG. 1B is a diagram showing a configuration of an exciting light irradiation means;

FIG. 2A is a sectional view showing a detection mechanism and a light irradiation part of fluorescence from an inspection sample in a capillary array and FIG. 2B is a diagram showing images on a CCD;

FIGS. 5A and 5B are graphs showing relationships between a distance between a lens optical axis and capillary and condensing efficiency in a fluorescence detection system;

FIG. 7 is a table comparing an embodiment and comparative examples of the capillary electrophoresis apparatus of the present invention;

FIG. 9A is a diagram illustrating a false peak and FIG. 9B is a graph showing the false peak;

DESCRIPTION OF THE PREFERRED EMBODIMENTS

Figure 3:
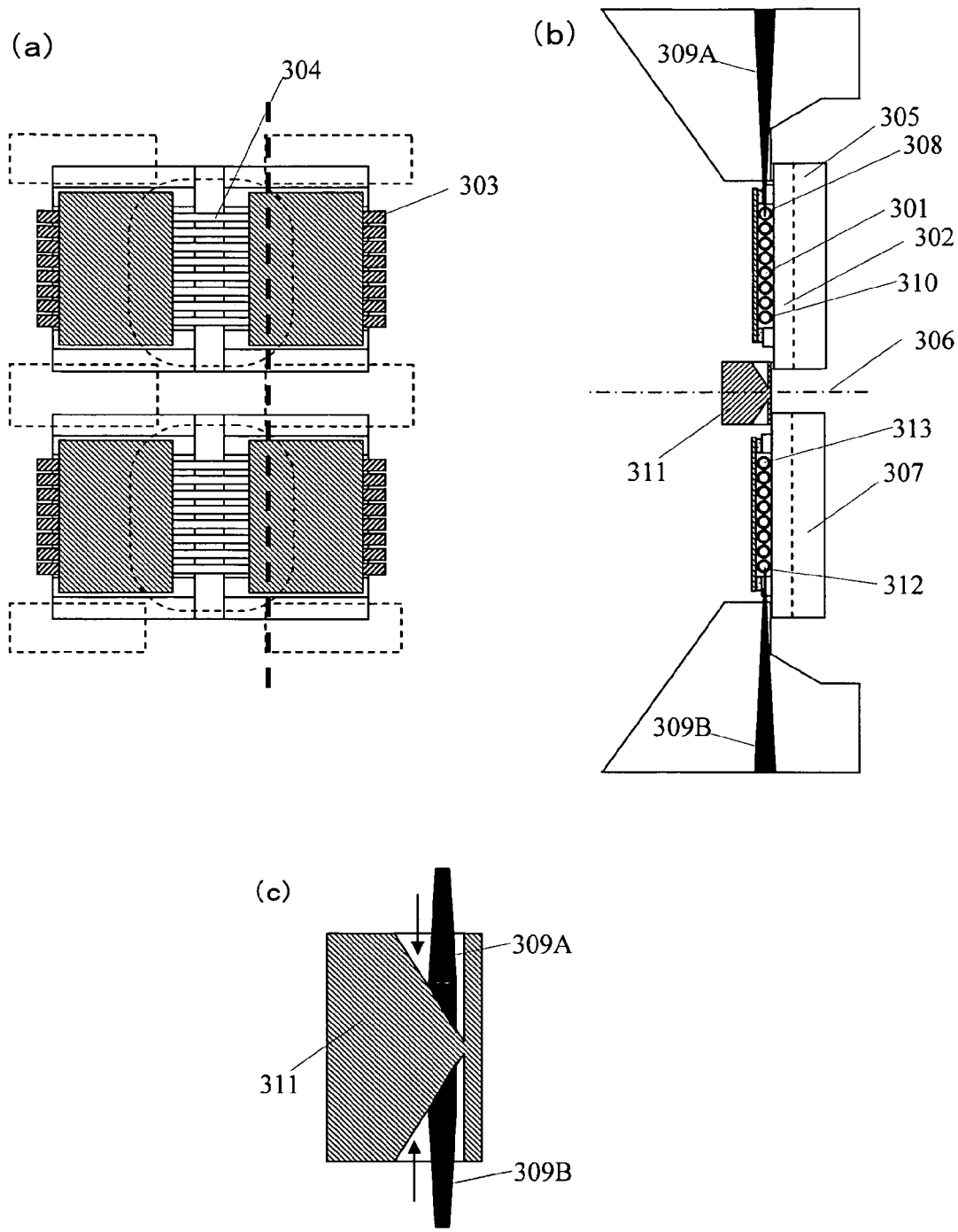
FIG. 3A is a front view showing the light irradiation/detection mechanism.
FIG. 3B is a sectional view thereof.
FIG. 3C is a sectional view showing a laser light cutoff part.

The above and other new features and advantages of the present invention will be described below with reference to drawings. However, such drawings are intended exclusively for description and do not limit the scope of the present invention.

FIG. 1A shows a schematic diagram of a capillary electrophoresis apparatus of the present invention. The capillary electrophoresis apparatus in the present invention (hereinafter referred to as "present apparatus") uses a plurality of capillaries in which a migration medium is filled up and analyzes sample components in a sample by introducing the sample into each capillary and separating such sample components by electrophoresis. Basic components of the present apparatus include a capillary array, optical unit of irradiation, optical unit of detection, auto sampler unit, migration medium filling unit, power unit, and temperature control unit.

A capillary array 101 is a removable replacement member including a plurality of capillaries 102 and is replaced with a new one when its quality declines and its resolution falls after performing analyses a predetermined number of times. By replacing the capillary array 101 of the capillaries 102 having a different length when changing the measuring technique, the length of the capillaries 102 can be adjusted. The capillary array 101 has a sample introduction part 104 for introducing samples into the capillaries 102, an irradiation part 103 for irradiating samples separated by migration with exciting light, and a capillary head 107 for bundling the capillaries.

The capillary 102 is a narrow tube having the inside diameter of several tens to several hundreds micrometer and the outside diameter of several hundreds micrometer and having surface coating to increase its strength. By filling the capillary 102 with a migration medium, a migration channel is formed. By applying a voltage to both ends of the migration channel, a sample can be separated by electrophoresis.

In the present embodiment, a quartz pipe whose external surface is polyimide-coated and having the total length of 47 cm, the outside diameter of 363 μm, and the inside diameter of 50 μm is used as the capillary 102. Incidentally, in the irradiation part 103 about 36 cm away from the sample introduction part 104, polyimide coating is removed to efficiently irradiate samples in the capillary 102 with exciting light. Eight capillaries 102 are bundled to form the capillary array 101. However, the number of capillaries 102 is not limited to eight and may be, for example, 2, 8, 16, 96, 192, 384, or the like. In addition, the capillary 102 may be coated with a resin other than polyimide if necessary.

The sample introduction part 104 arranges a sample introduction end 105 of the capillary 102 by fitting to a well of a sample container and can introduce a plurality of samples held in each well into the migration channel.

In the present embodiment, the sample introduction end 105 is formed by inserting a tip of the capillary 102 into a hollow electrode to constitute the sample introduction part 104. The tip of the capillary 102 at the sample introduction end 105 slightly projects from the hollow electrode. The hollow electrode made of a stainless pipe is electrically connected to a high-voltage power supply. A sample can be introduced into the capillary through electrophoresis by soaking the sample introduction end 105 in the sample and applying a voltage. However, the method of introducing a sample is not limited to electrophoresis and a sample may be introduced into the migration channel by pressure, distributive pouring, or the like.

The irradiation part 103 is a part that irradiates a migration medium filled in the capillary 102 with exciting light and can irradiate sample components separated by electrophoresis with exciting light. A phosphor labeled on a sample component emits light of a wavelength depending on the sample component.

An optical system of the capillary electrophoresis apparatus includes a light source, a detection part 118 including the irradiation part 103, and a detection mechanism for detecting fluorescence generated by the detection part. The light source oscillates a laser light 109 (lights of 488.0 nm and 514.5 nm from an argon ion laser), which is a coherent light. In the detection part 118, the irradiation parts 103, which are a location of the capillary through which the laser light 109 is transmitted, are arranged in parallel. Then, the detection part 118 is irradiated with the laser light 109 from both upper and lower directions in such a way as to pass through the irradiation parts 103 of a plurality of capillaries simultaneously. The laser light 109 excites an inspection sample so that fluorescence is emitted from the inspection sample. By detecting the fluorescence by means of the detection mechanism (FIG. 2) including a CCD 204, information depending on the inspection sample such as DNA molecular arrangement can be obtained.

The irradiation part 103 radiates exciting light by means of, for example, the exciting light irradiation means shown in FIG. 1B. The exciting light, which is a laser light or beam emitted from a laser light source 170 is split into two by a beam splitter 171 and two split laser lights 109 are reflected by exciting light irradiation means such as mirrors or reflectors 172 before being incident on each capillary array from mutually opposite directions. The laser lights 109 are condensed by laser condensing lenses 173 before being radiated on the irradiation part 103 of the capillary array from one side of each capillary array. After passing through each capillary array, the laser lights 109 hit a laser light cutoff part 311.

First Embodiment

FIG. 2A shows a detection mechanism of fluorescence from an inspection sample in a capillary array in a first embodiment and the irradiation part 103. The detection mechanism includes a fluorescence condensing lens 201, an optical filter 209, a grating 202, a focusing lens 203, and the CCD 204. After passing through the optical filter 209 to remove exciting light, fluorescence 205 from an inspection sample in the capillary 102 generated by the laser light 109 is radiated on the irradiation part 103 made an approximately parallel light 206 by the fluorescence condensing lens 201, dispersed into a spectrum by the grating 202 before being formed as images on the CCD 204 by the focusing lens 203. FIG. 2B shows such images on the CCD. 16 capillary images are arranged in the Y axis direction and light emission 208 from each capillary is dispersed in the X axis direction.

The capillary head 107 bundles eight capillaries to hold them and can be removed from the main body of the apparatus. The capillary head 107 can be connected to a polymer filling block 152 by pressure-resistant airtightness. Then, the capillary 102 can be filled with a new migration medium by a migration medium filling unit from an end part 108.

The auto sampler unit is a mechanism to transport various containers including a sample container used for electrophoretic analysis to a predetermined position immediately below the sample introduction part 104 to hold them. The auto sampler unit in the present embodiment transports a sample container, a buffer container, a washing container, and a waste fluid container by means of a robot arm equipped with claws.

The robot arm is equipped with claws for fixing each container thereon and can move three-dimensionally. Accordingly, each container stored at the predetermined position can be transported to immediately below the sample introduction part 104 and held there for a predetermined time before being returned to the predetermined position.

The buffer container is a container for holding a buffer solution in which the sample introduction end 105 is soaked. The buffer container is transported to immediately below the sample introduction part 104 during electrophoretic analysis so that the sample introduction end 105 is soaked in the buffer solution. Also when the apparatus is on standby, the buffer container is transported just like during electrophoretic analysis so that the sample introduction end 105 is soaked in the buffer solution to prevent the migration medium in the capillary 102 from drying.

The washing container is a container for holding a cleaning fluid for washing the sample introduction end 105 and is transported to immediately below the sample introduction part 104 during migration medium filling, preliminary migration, and after sample introduction. By soaking the sample introduction end 105 in the cleaning fluid in the washing container, the sample introduction end 105 can be washed to avoid contamination.

The waste fluid container is a container for holding a used migration medium and is transported to immediately below the sample introduction part 104 during migration medium filling to accept a used migration medium discharged from the sample introduction part 104 during migration medium filling.

The sample container is a container for holding a plurality of micro samples and is transported to immediately below the sample introduction part 104 during sample introduction. In the present embodiment, the sample container is constructed by putting a receptor, which is a resin sheet, on a sample plate equipped with 24-row/16-column wells capable of holding several tens µl of sample and sandwiching the receptor between a holder and clip. The sample includes, for example, a solution containing nucleic acids fluorescence-labeled so that four types of nucleoside base molecules are identified and having many suitable lengths (sizes). The receptor has a through hole normally in a sealed state at a position corresponding to a well to enable contact of the sample introduction end 105 and a sample when the sample is introduced while preventing evaporation of the sample in the well. Moreover, evaporation of the sample can also be prevented by attaching a protective film to a top surface of the receptor. The holder and clip are integrated by sandwiching a sample plate or receptor between them to form a sample container that can be transported by a robot arm.

The migration medium filling unit is a mechanism for filling the capillary 102 with a polymer, which is a migration medium. The migration medium filling unit in the present embodiment includes the polymer filling block 152, a syringe 153, a tube 155, and an electromagnetic valve 156 and can automatically fill the capillary 102 with a new migration medium before starting an analysis.

The polymer filling block 152 has a polymer channel 154 and connects the syringe 153 and the tube 155, and the capillary head 107 can be attached to/detached from the polymer filling block 152. The capillary head 107 is mounted to the polymer filling block 152 while maintaining pressure-resistant airtightness. The polymer channel 154 communicate the syringe 153 filled with the migration medium and the tube 155 equipped with the electromagnetic valve 156. The other end of the tube 155 is soaked in a buffer solution held in an anode buffer container 163.

To fill the capillary 102 with a migration medium, the waste fluid container is arranged immediately below the sample introduction part 104, the electromagnetic valve 156 is closed, and a plunger of the syringe 153 is pushed. The migration medium in the syringe 153 is thereby caused to flow from the end part 108 into the capillary 102 via the polymer channel 154. The used migration medium in the capillary 102 is discharged from the sample introduction end 105 before being accepted by the waste liquid container.

The power unit is a mechanism to apply a voltage to a migration channel constituted by the migration medium in the capillary 102 and can cause electrophoresis of samples. The power unit in the present embodiment is electrically connected to the hollow electrode of the sample introduction part 104 and an anode electrode 164 and includes a high-voltage power supply capable of generating a high voltage of about 15 kV.

When a sample is introduced, the capillary 102, the polymer channel 154, and the tube 155 are filled with a migration medium, the sample introduction end 105 is soaked in a sample held in a well of the sample container, and the electromagnetic valve 156 is opened. Accordingly, a current-carrying channel consisting of the hollow electrode of the sample introduction part 104, sample in the well, capillary 102, polymer channel 154, tube 155, buffer solution in the anode buffer container 163, and anode electrode 164 is formed. Then, a pulse voltage is applied to the current-carrying channel with the hollow electrode of the sample introduction part 104 at a negative potential and the anode electrode 164 at a positive potential. Negatively charged sample components present in the well, for example, DNA migrate thereby from the sample introduction end 105 to the migration channel.

In contrast to when a sample is introduced, the sample introduction end 105 is soaked in a buffer solution held in the buffer container during migration analysis. A current-carrying channel consisting of the hollow electrode of the sample introduction part 104, buffer solution in the buffer container, capillary 102, polymer channel 154, tube 155, buffer solution in the anode buffer container 163, and anode electrode 164 is formed. Then, in contrast to when a sample is introduced, a high voltage of about 15 kV is applied. An electric field is thereby generated in a direction from the irradiation part 103 to the sample introduction part 104 so that negatively charged sample components introduced into the migration channel migrate in the direction of the irradiation part 103.

The temperature control unit is a mechanism to control the temperature of the migration channel affecting the migration speed of sample components. The temperature control unit in the present embodiment houses the capillaries 102 in a thermostatic oven 130. Then, the capillaries 102 are maintained at a predetermined temperature by circulating air at a constant temperature maintained by a temperature control mechanism such as a Peltier device through the thermostatic oven by means of a ventilation mechanism such as a fan.

A basic procedure for electrophoretic analysis will be described below. The basic procedure for electrophoretic analysis is roughly divided into preparations, migration medium filling, preliminary migration, sample introduction, and migration analysis. Samples or reagents are set to the present apparatus by an operator of the present apparatus as preparations before starting an analysis. More specifically, first the buffer container and the anode buffer container 163 are filled with a buffer solution forming a portion of the current-carrying channel. The buffer solution is, for example, an electrolytic solution for electrolysis commercially available from various companies.

Also, samples to be analyzed are distributively poured into wells in the sample container. Samples are, for example, PCR (Polymerase chain reaction) products of DNA. A cleaning fluid for washing the sample introduction part 104 is also poured into the washing container. The cleaning fluid is, for example, pure water. A separation medium used for electrophoresis of sample is also poured into the syringe 153. The separation medium is, for example, polyacrylamide based separation gel for electrolysis commercially available from various companies. Further, if degradation of the capillary 102 is anticipated or the length of the capillary 102 should be changed, the capillary array 101 is replaced. Then, after preparations are completed, the operator operates the present apparatus to start the analysis.

First, migration medium filling is performed. This is a step of filling the capillary 102 with a new migration medium to form a migration channel. In the migration medium filling in the present embodiment, first a waste fluid container is transported by the auto sampler unit to immediately below the sample introduction part 104 so that a used migration medium discharged from the sample introduction end 105 can be accepted. Then, the syringe 153 is driven to fill the capillary 102 with a new migration medium and to discard the used migration medium. Lastly, the sample introduction end 105 is soaked in the cleaning fluid in the washing container to wash the sample introduction end 105 contaminated by the migration medium.

Next, preliminary migration is performed. This is a step of making the migration medium fit for electrophoresis by applying a predetermined voltage to the migration medium. In the preliminary migration in the present embodiment, first the sample introduction end 105 is soaked in the buffer solution in the buffer container by the auto sampler unit to form a current-carrying channel. Then, a voltage of about several kV to several tens kV is applied to the migration medium by the power unit for several min to several tens min to make the migration medium fit for electrophoresis. Lastly, the sample introduction end 105 is soaked in the cleaning fluid in the washing container to wash the sample introduction end 105 contaminated by the buffer solution.

Next, a sample is introduced. This is a step of introducing sample components into the migration channel. In the sample introduction in the present embodiment, first the sample introduction end 105 is soaked in the sample held in a well in the sample container by the auto sampler unit. A current-carrying channel is thereby formed so that sample components can be introduced into the migration channel. Then, sample components are introduced into the migration channel by applying a pulse voltage to the current-carrying channel by means of the power unit. Lastly, the sample introduction end 105 is soaked in the cleaning fluid in the washing container to wash the sample introduction end 105 contaminated by the sample.

Next, migration analysis is performed. This is a step of separating and analyzing each sample component contained in the sample by electrophoresis. In the migration analysis in the present embodiment, first the sample introduction end 105 is soaked in the buffer solution in the buffer container by the auto sampler unit to form a current-carrying channel. Then, an electric field is generated in the migration channel by applying a high voltage of about 15 kV to the current-carrying channel by means of the power unit. Each sample component in the migration channel migrates due to the generated electric field to the irradiation part 103 at a speed depending on properties of each sample component. That is, sample components are separated based on differences of migration speed. Then, sample components are detected in order of arrival at the irradiation part 103. If, for example, the sample contains many DNAs having different base lengths, differences in migration speed arise due to base lengths with DNAs arriving at the irradiation part 103 in order of ascending length. If a fluorescent substance depending on a terminal base sequence is attached to each DNA, the terminal base sequence can be detected in order of arrival at the irradiation part 103. Then, when planned data is obtained, the applied voltage is stopped to complete the migration analysis.

The above is a series of analysis procedure. To perform further analysis, the analysis procedure is started from the step of migration medium filling.

Light irradiation/detection, which is a characteristic mechanism of the present invention, will be described below with reference to FIG. 3. FIG. 3A is a front view showing the light irradiation/detection mechanism and FIG. 3B is a side view thereof. In the present embodiment, eight capillaries 301 are arranged on a glass substrate 302. On the glass substrate 302, the capillaries 301 are arranged substantially in parallel with the glass substrate 302. Also, removed portions 304 of a polyimide coating 303 in each capillary 301 are arranged in a straight line.

A capillary array A 305 is arranged so as to be positioned above a condensing lens optical axis 306. A capillary array B 307 is arranged so as to be positioned below the condensing lens optical axis 306. The positional relationship between the two capillary arrays is not limited to above/below the condensing lens optical axis 306, as shown in the present embodiment, and the two capillary arrays may be positioned, for example, to the left and right of the condensing lens optical axis 306 as long as they are positioned approximately symmetrically with respect to the condensing lens optical axis 306.

A capillary 308 at the upper end of capillaries in the capillary array A 305 is irradiated with a laser light 309A and the laser light 309A successively propagates from one capillary to the adjacent one to cross the eight capillaries of the capillary array A 305. After crossing an eighth capillary 310, the laser light 309A hits the laser light cutoff part 311 so that the laser light 309A does not propagate to capillaries in the capillary array B 307.

A capillary 312 at the lower end of capillaries in the capillary array B 307 is irradiated with a laser light 309B and the laser light 309B successively propagates from one capillary to the adjacent one to cross the eight capillaries of the capillary array B 307. After crossing an eighth capillary 313, the laser light 309B hits the laser light cutoff part 311 so that the laser light 309B does not propagate to capillaries in the capillary array A 305.

The laser light cutoff part 311 in the present embodiment uses copper whose surface is reduction-treated. Material/surface treatment of the laser light cutoff part 311 is not limited to this and a challenge required of material/surface treatment of the laser light cutoff part is to absorb a laser light hitting here in such a way that the laser light should not become a stray light of the optical system and to minimize scattering of the laser light. In addition, it is desirable that reflectance properties of laser light do not change with time. Materials satisfying such conditions can be used as materials for the laser light cutoff part. For example, copper whose surface is blackening-treated or black anodized aluminum may be used. Moreover, as shown in FIG. 3C, inclined surfaces are formed in the laser light cutoff part to prevent reflection of laser light in the direction of capillaries so that the laser light does not hit the laser light cutoff part 311 vertically.

Figure 4:
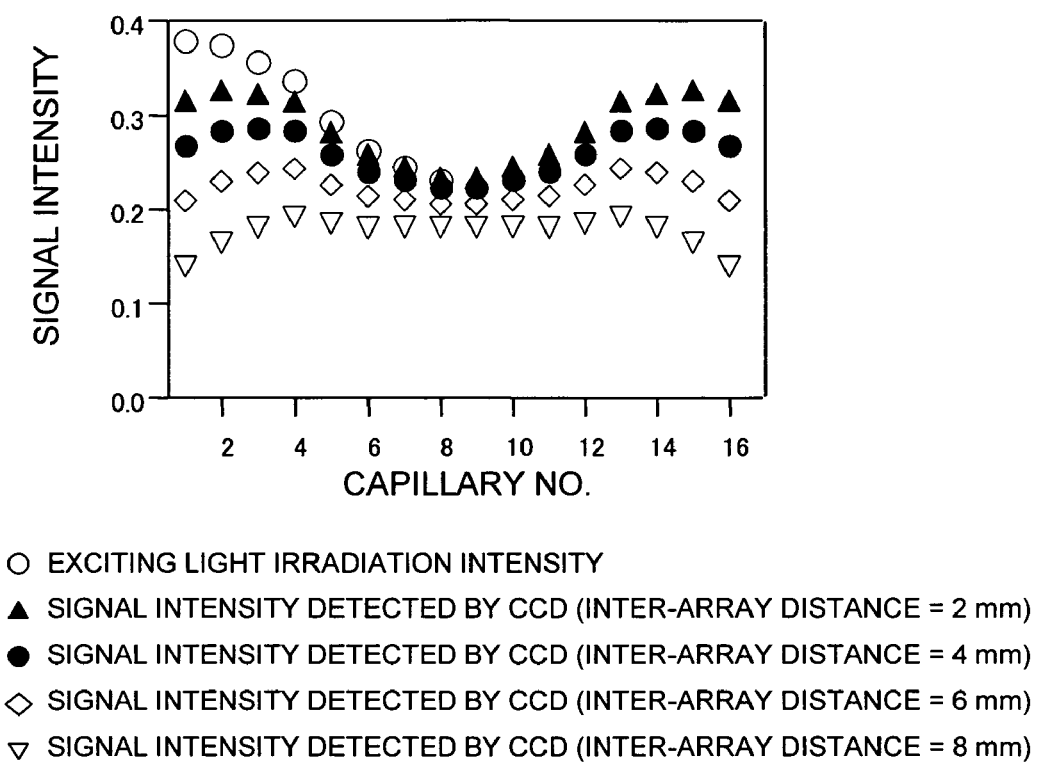
FIG. 4 is a graph showing irradiation light intensity distribution of capillaries.

The capillary has the capillary outside diameter of 363 μm, the quartz outside diameter of 323 μm, and the quartz inside diameter of 50 μm and has a separation medium whose index of refraction is 1.41 injected into the tube. In a process of propagation of exciting laser light from one capillary to another, a reflection loss of the laser light is produced on the outside diameter of the capillary based on a difference of the index of refraction between quartz and air. Therefore, the distribution of irradiation light intensity of eight capillaries in the capillary array A 305 is as shown in FIG. 4. Since the laser light is radiated from one side, irradiation light intensity is not uniform. The dispersion of signal intensity (standard deviation/average value) among eight capillaries in a capillary array is wide with 0.19.

FIG. 5 shows relationships between the distance between a lens optical axis 220 and capillary and condensing efficiency in the fluorescence detection system shown in FIG. 2. With the increasing distance between the capillary and the lens optical axis 220, as shown in FIG. 5, signal intensity reaching the CCD 204, which is an optical detection means, lessens. This is because, as the capillary moves away from the lens optical axis 220, a propagation angle 221 of fluorescence to the CCD increases, leading to "vignetting" in the lens system in which part of fluorescence is lost without reaching the CCD.

Here, the distance between the capillaries 310 and 313 nearest to the lens optical axis 306 in the two capillary arrays A and B respectively is defined as an inter-array distance (In the present embodiment, the inter-array distance will be double the distance between the lens optical axis 306 and the capillary 310 or 313, which are the nearest to the lens optical axis).

Intensity of signal light of each capillary formed on the CCD before being detected is obtained as a product of exciting light irradiation intensity and condensing efficiency and looks as shown in FIG. 5. FIG. 5A shows a case in which the inter-array distance is 2 mm. The ratio of min signal intensity/max signal intensity among eight capillaries of the capillary array A is 0.72, significantly improving 0.61 described above.

FIG. 5B shows a case in which the distance between the capillary nearest to the lens optical axis in each of the capillary arrays A and B and the lens optical axis is 2 mm. The dispersion of signal intensity (standard deviation/average value) among 16 capillaries in the capillary arrays is 0.13, improving significantly compared with the above case.

Since signal intensity of the other remaining capillary array is similar, signal intensity of 16 capillaries in a state in which two capillary arrays are set will be uniform, as shown in FIG. 4.

Figure 6:
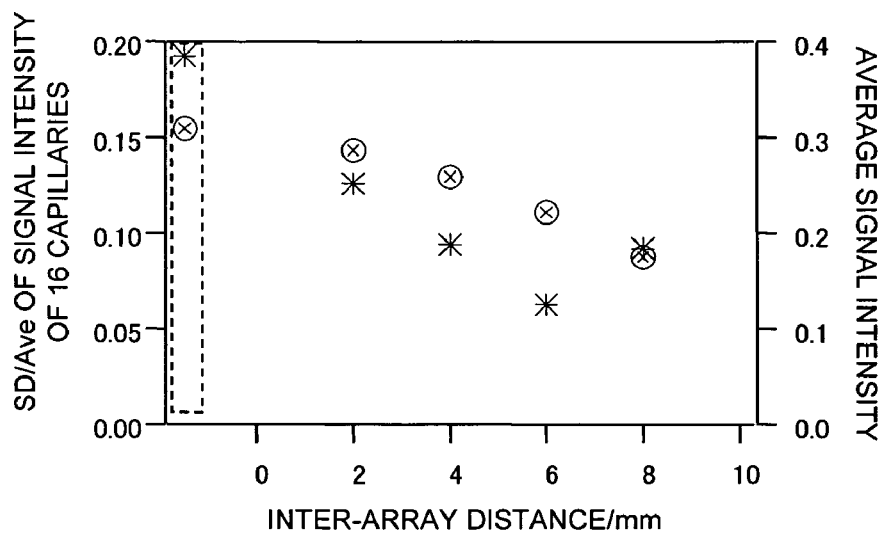
FIG. 6 is a graph showing relationships between variations/average value of signal intensity of 16 capillaries and the distance between arrays.

As shown in FIG. 6, an optimal value of the inter-array distance exists for the dispersion of signal intensity (standard deviation/average value) of 16 capillaries with a minimum value when the inter-array distance is 6 mm. On the other hand, the average value of 16 capillaries will decrease as the inter-array distance increases. When two arrays are simultaneously detected by one CCD, a larger CCD will be needed as the inter-array distance increases, creating a disadvantage of increasing apparatus costs. The inter-array distance is determined by considering the dispersion of signal intensity (standard deviation/average value) of 16 capillaries, average value, and apparatus costs. In the present embodiment, the inter-array distance was set to 4 mm with the specifications for the apparatus that the dispersion of signal intensity (standard deviation/average value) of 16 capillaries is 0.1 or less. 16 capillary images will be about 10 mm (arrangement pitch 370 μm×16+4 mm) in the capillary arrangement direction and a CCD covering such images is used.

As a comparative example of the present example, as shown in FIG. 7, a system in which the capillary arrays A and B, each consisting of eight capillaries, are independently removable and are each irradiated with two exciting irradiation lights from both sides, with each exciting irradiation light passing through 16 capillaries is examined (2-array double-sided through irradiation method). Also, a system in which the capillary array A is irradiated with one of two laser lights and the capillary array B irradiated with the other laser light, each from one side, and the positional relationship between the lens optical axis and capillary arrays is considered is examined.

The first point is signal intensity. Laser light is caused to pass through 16 capillaries in the 2-array double-sided through irradiation and therefore, signal intensity can be made maximum. The second point is the dispersion of signal intensity. In the single-sided irradiation, the dispersion of signal intensity will spread more depending on the positional relationship between the capillary arrays and lens optical axis.

Figure 8:
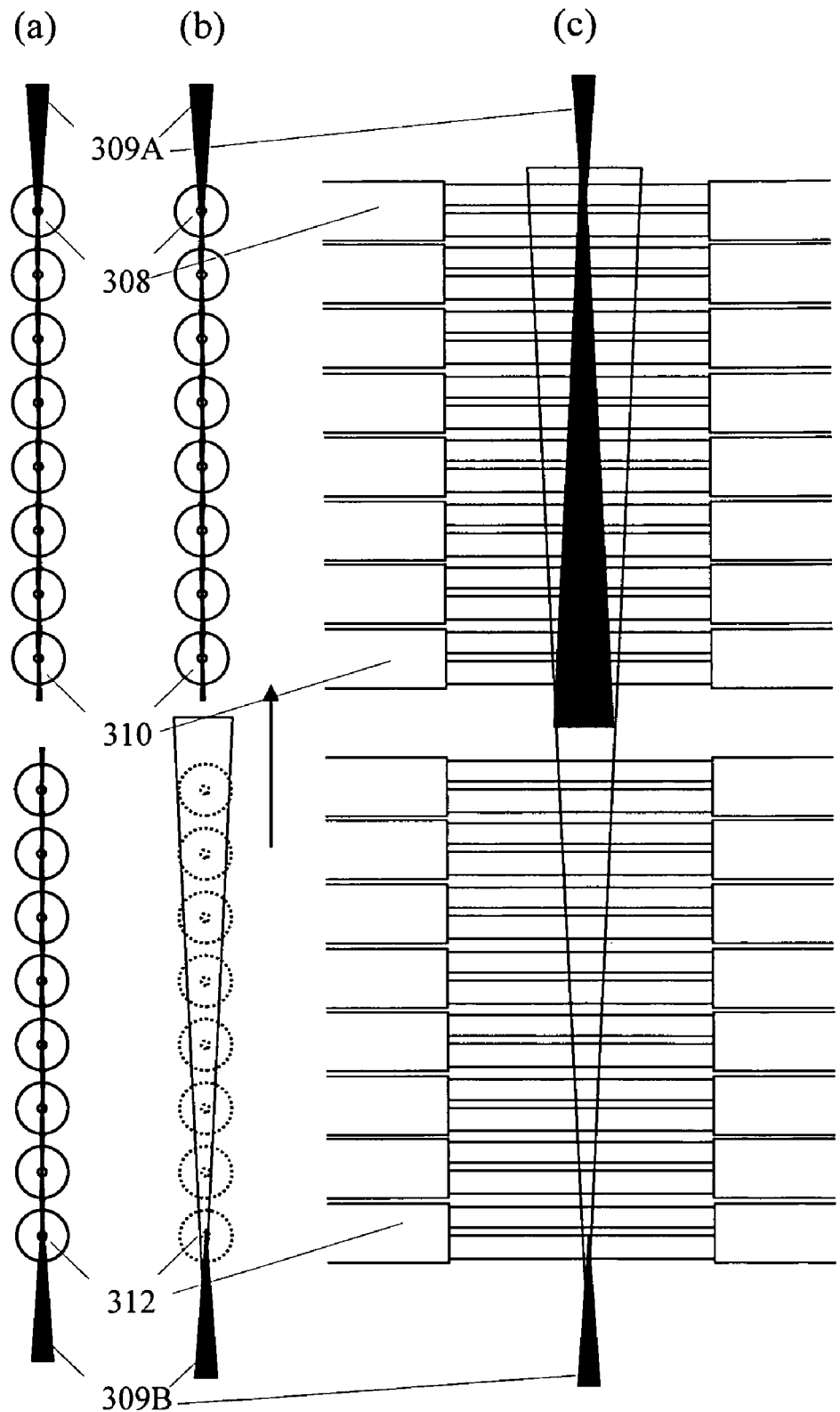
FIGS. 8A to 8C are diagrams showing beam widths of exciting irradiation light.

The third point is the signal-to-noise ratio when one array is used. The beam width of exciting irradiation light in a capillary cross section of 2-array double-sided through irradiation will be described using FIG. 3 and FIG. 8. As described in Japanese Patent Application Laid-Open No. 2004-144479, it is desirable to adjust the focus of the laser light 309A on the first capillary 308 by stopping down the lens to cause the laser light 309A to propagate efficiently (FIG. 8A). Therefore, the focal position is adjusted to the first capillary 308 in the capillary array A 305 and the first capillary 312 in the capillary array B 307. When viewed in a plane including a capillary cross section, the width of exciting irradiation light propagates through the capillary array by repeating convergence/divergence due to a lens effect of capillaries. If, here, the capillary array B 307 is removed from the apparatus (FIG. 8B), the lens effect of the capillary array B 307 disappears and thus, the beam diameter of the exciting irradiation light 309B from below becomes large when it reaches the eighth capillary 310 of the capillary array A 305. If a point apart from the central axis of the capillary is irradiated with exciting light without the exciting irradiation light being sufficiently narrowed down when being incident on a capillary, it is difficult for the exciting light to pass through the inside diameter of the capillary, not contributing greatly to signal generation. On the other hand, the exciting light contributes to scattering, which is a noise generation source. Therefore, there is a problem in the 16-capillary double-sided through irradiation that the signal-to-noise ratio falls when one capillary array is removed. In the present invention, on the other hand, even if one capillary array is removed, the signal-to-noise ratio of the remaining capillary array does not fall.

The fourth point is a false peak. The beam width of exciting irradiation light in the capillary axis direction will be described in detail using FIG. 8C. Since there is no lens effect of capillary in the capillary axis direction, as shown in FIG. 8C, the width of exciting irradiation light becomes wider as the light propagates through the capillary array. In the fluorescence detection system shown in FIG. 2, a plurality of light irradiation parts of capillary are arranged on the Y axis and thus, a marked line of grating is in a direction along the Y axis and light emission from the capillaries is dispersed in the X axis direction. With such a configuration of the detector, as shown in FIG. 9A, when DNA bands 901 separated by electrophoresis based on lengths pass by an exciting light 903 condensed by a capillary 902 and having a certain width, the wavelength of an emission spectrum 904 is seemingly changed by migration of an emission image on the CCD in the capillary axis direction, that is, the wavelength dispersion direction due to an effect that an emission point migrates within the exciting light width. Effectually, an effect similar to that when the wavelength of the emission spectrum changes with time while crossing exciting light is gained. If, in one use of electrophoresis in which a plurality of types of fluorochrome are used and each type of fluorochrome is associated with four types of bases, the emission spectrum seemingly changes, it becomes difficult to completely associate observed emission spectra with various types of fluorochrome or various types of bases. That is, when emission spectrum components are associated with various types of bases, residual components (false peak) that cannot be associated arise. As shown in FIG. 8C, the laser beam diameter can be made smaller in the present embodiment compared with the double-sided through irradiation. The above false peak can thereby be reduced.

The fifth point is a problem of returned light to the light source of exciting irradiation light. Japanese Patent Application Laid-Open No. 2004-144479 shows a problem of laser light intensity destabilized by laser light being returned to a laser cavity. Since the present invention substantially concerns single-sided irradiation, there is an advantage that such a problem does not exist.

The sixth point is the number of fluorescence condensing systems. If, in the configuration of 2-array single-sided irradiation, two capillary arrays are arranged in such a way that images of the capillary arrays are detected by one fluorescence detection system, the two capillary arrays mechanically interfere. To prevent two arrays from colliding with each other, it is unavoidable to provide two fluorescence detection systems.

In the present embodiment, as described above, the following i to v can be realized by attaching two capillary arrays of single-sided irradiation, each including eight capillaries:

i) Capillaries can be attached/detached in units of eight capillaries, though the system is a 16-capillary array system.

ii) Even if one capillary array is removed, the signal-to-noise ratio of the remaining capillary array does not fall.

iii) Even if capillaries of one 8-capillary array contain air without a separation medium being injected, the remaining capillaries can properly be irradiated with light.

iv) A problem of laser light intensity being destabilized due to laser light returned to a laser cavity does not arise.

v) False peaks can be reduced by the laser beaming diameter substantially being made smaller.

As has been described above, a capillary electrophoresis apparatus in the present invention includes electrophoresis in which, for example, a plurality of types of fluorochrome are associated with various bases and the light irradiation method by which capillaries at both ends of a capillary array in which a plurality of capillaries are arranged on a plane substrate are irradiated with laser light and the laser light successively propagates from one capillary to the adjacent capillary, wherein the number of attached capillary arrays can be changed depending on the number of samples. Though laser irradiation in the present invention uses two beams, single-sided irradiation to the capillary arrays is substantially adopted. In the laser light single-sided irradiation, a problem generally arises that irradiation light intensity of laser light widely varies inside the capillary array. Irradiation light intensity becomes larger on the laser light incoming side and smaller on the laser light outgoing side. Challenges of being able to attach two capillary arrays separately and unevenness of irradiation intensity can simultaneously be solved. Moreover, since single-sided irradiation is substantially adopted, a problem of laser light intensity destabilized by laser light being returned to a laser cavity does not arise.

Second Embodiment

Figure 10:
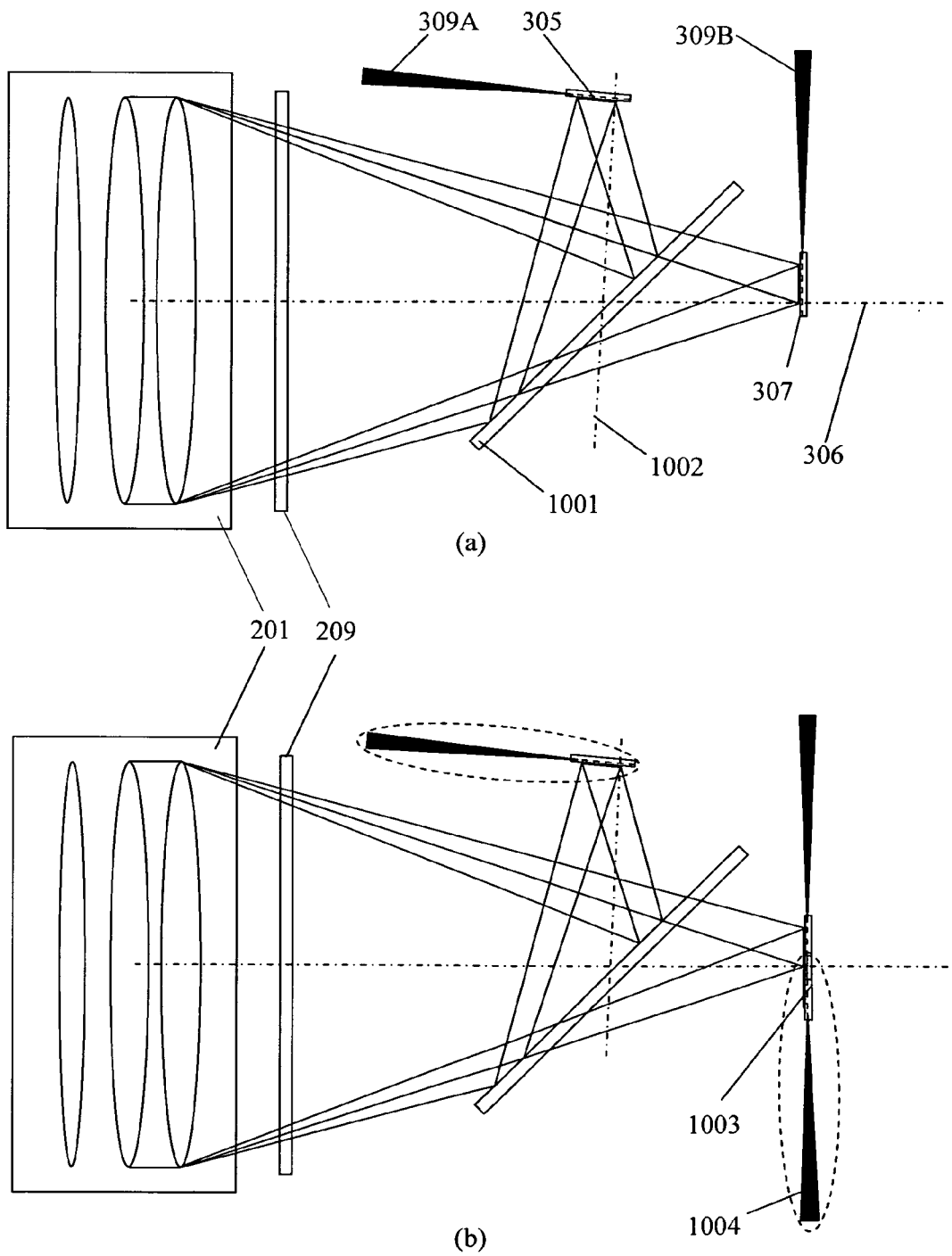
FIG. 10A is a schematic diagram of a second embodiment of the capillary electrophoresis apparatus of the present invention and FIG. 10B is a diagram illustrating a mirror image for a half mirror of a capillary array A.

Another embodiment is shown in FIGS. 10A and 10B. The second embodiment is another embodiment of the first embodiment shown in FIG. 2. Main differences from the first embodiment include: i) a half mirror 1001 exists in the fluorescence detection system and ii) two capillary arrays are neither coplanar and nor adjacent to each other. The half mirror 1001 has properties of 50% transmission and 50% reflection in a fluorescence wavelength area. The half mirror 1001 reflects fluorescence emitted from the capillary array A 305 to guide it to a CCD and also transmits fluorescence emitted from the capillary array B 307 to guide it to the CCD. Since, in the second embodiment, the optical system from the fluorescence condensing lens to the CCD is the same as that shown in FIG. 2, a portion from the fluorescence condensing lens to the CCD is omitted in FIG. 10. An illustration of a capillary array mounting member is also omitted in FIG. 10.

In FIG. 10B, portions indicated by broken line ellipses are mirror images of the capillary array A 305 with respect to the half mirror 1001. Numeral 1002 shows a mirror image of the condensing lens optical axis with respect to the half mirror, numeral 1003 shows a mirror image of the capillary array A with respect to the half mirror, and numeral 1004 is a mirror image of laser light incident on the capillary array A with respect to the half mirror. As is evident from FIG. 10B, the second embodiment has an optical system substantially the same as that shown in FIG. 2. Though, in the second embodiment, fluorescence, which is a signal light, is reduced to 50% intensity by the half mirror 1001, there is no need to arrange two capillary arrays next to each other so that two capillary array mounting mechanisms can be arranged with sufficient space. There is also an advantage that there is no need to arrange the laser light cutoff part shown in FIG. 3 in a narrow space between adjacent capillary arrays. In the second embodiment, with a plurality of half mirrors arranged, the number of capillary arrays is not limited to two and three or more capillary arrays can be arranged.

Third Embodiment

Figure 11:
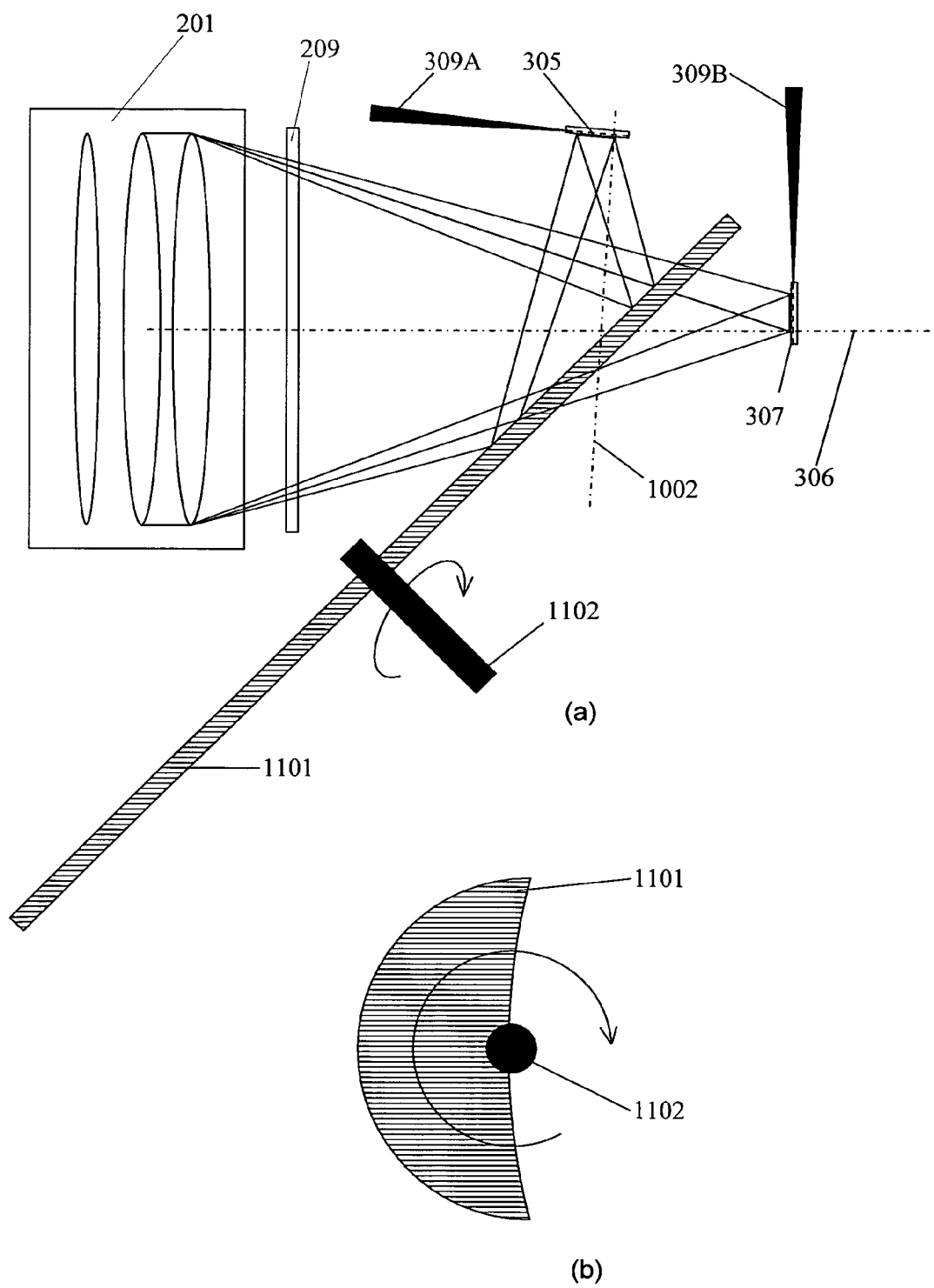
FIG. 11A is a schematic diagram of a third embodiment of the capillary electrophoresis apparatus of the present invention and FIG. 11B is a diagram showing a semicircular mirror.

Still another embodiment is shown in FIG. 11A. The third embodiment is another embodiment of the second embodiment shown in FIG. 10. Instead of the half mirror, a rotating semicircular mirror is used. The semicircular mirror has a structure in which a rotating mirror part 1101 rotates around a rotating mirror axis 1102. FIG. 11B is a plan view of the semicircular mirror. A signal from the capillary array A 305 and that from the capillary array B 307 are alternately acquired by a CCD (not shown). As a result, while the time required to acquire signals is reduced to about half that of the second embodiment, signal intensity equivalent to that in the second embodiment can be acquired because, without using a half mirror, there is no loss of signal fluorescence by the half mirror. Similar to the second embodiment, there is no need to arrange two capillary arrays next to each other so that two capillary array mounting mechanisms can be arranged with sufficient space. There is also an advantage that there is no need to arrange the laser light cutoff part shown in FIG. 3 in a narrow space between adjacent capillary arrays. In the third embodiment, with a plurality of rotating mirrors arranged, the number of capillary arrays is not limited to two and three or more capillary arrays can be arranged.

The present invention can be used for a capillary electrophoresis apparatus.

What is claimed is:

1. A capillary electrophoresis apparatus; comprising:
a single exciting light source;
two capillary arrays, each consisting of a plurality of capillaries having irradiated parts adapted to be irradiated with exciting light and arranged in parallel on a plane in such a way that the irradiated parts of capillaries contained in each array are arranged in parallel with each other on the same plane;
a beam splitter configured to split light from the single exciting light source;
a first reflector configured to lead a first light from the beam splitter in a first direction to a first irradiated part, and second and third reflectors configured to lead a second light from the beam splitter to a second irradiated part from a second direction mutually opposite to the first direction, wherein, each of the reflectors is adapted to irradiate the irradiated parts with exciting light in such a manner that the exciting light passes through the irradiated parts of all the capillaries included in a respective capillary array;
light cutoff means arranged between the irradiated parts of the capillaries of the two capillary arrays, wherein the light cutoff means is configured to prevent light from entering an adjacent capillary array;
and
one optical detection system arranged in a direction perpendicular to a plane where the irradiated parts of the capillaries contained in the two capillary arrays are arranged, the optical detection system being adapted to detect light emission generated by the capillaries contained in the two capillary arrays,
wherein:
each of the capillary arrays is individually removable,
the irradiated parts of the two capillary arrays are positioned across an optical transmission central axis of the optical detection system as viewed from above, such that one irradiated part is positioned on one side of the central axis and another irradiated part is positioned on the other side of the central axis,
the light cutoff means prevents transmitted light that has traveled through one of the capillary arrays from entering the other of the capillary arrays,
in simultaneously detecting light emission at the optical detection system, both of the capillary arrays are in a state where they are fixed to the capillary electrophoresis apparatus, and
signal intensities of all of the capillaries used for measurement vary by 0.13 or less.

2. The capillary electrophoresis apparatus according to claim 1, wherein inclined surfaces are formed in portions of the light cutoff means where the exciting light of said light cutoff means hits.

3. A capillary electrophoresis apparatus from which two capillary arrays, each consisting of a plurality of capillaries having irradiated parts adapted to be irradiated with exciting light and arranged in parallel on a plane, can independently be removed in such a way that the irradiated parts of the capillaries contained in each array are arranged in parallel with each other on the same plane; comprising:
a single exciting light source;
a mounting surface on which the irradiated parts of capillaries of the two capillary arrays are mounted so as to be arranged in parallel with each other and on the same plane;
a beam splitter configured to split light from the single exciting light source;
a first reflector configured to lead a first light from the beam splitter in a first direction to a first irradiated part, and second and third reflectors configured to lead a second light from the beam splitter to a second irradiated part from a second direction mutually opposite to the first direction, wherein, each of the reflectors is adapted to irradiate the irradiated parts with exciting light in such a manner that the exciting light passes through the irradiated parts of all the capillaries included in a respective capillary array;
light cutoff means arranged between mounting positions of the irradiated parts of the capillaries of the two capillary arrays on the mounting surface;
and
one optical detection system arranged in a direction perpendicular to the mounting surface of the two capillary arrays, the optical detection system being adapted to simultaneously detect light emission generated by capillaries in said two capillary arrays mounted on the capillary electrophoresis apparatus,
wherein:
each of the capillary arrays is individually removable,
the optical detection system simultaneously detects light emission generated by all of the capillaries used for measurement,
the irradiated parts of the two capillary arrays are mounted at locations positioned across an optical transmission central axis of the optical detection system, as viewed from above, such that one irradiated part is positioned on one side of the central axis and another irradiated part is positioned on the other side of the central axis,
the light cutoff means prevents transmitted light that has traveled through one of the capillary arrays from entering the other of the capillary arrays,
in simultaneously detecting light emission at the optical detection system, both of the capillary arrays are in a state where they are fixed to the capillary electrophoresis apparatus, and
signal intensities of all of the capillaries used for measurement vary by 0.13 or less.

4. The capillary electrophoresis apparatus according to claim 3, wherein inclined surfaces are formed in portions of the light cutoff means where the exciting light of said light cutoff means hits.

5. A method, comprising:
arranging two capillary arrays, each consisting of a plurality of capillaries having irradiated parts adapted to be irradiated with exciting light and arranged in parallel on a plane in such a way that the irradiated parts of the capillaries of respective capillary arrays are arranged in parallel with each other on the same plane across a light cutoff means;
splitting light from a single exciting light source using a beam splitter;
leading a first light from the beam splitter in a first direction to a first irradiated part using a first reflector, and leading a second light from the beam splitter to a second irradiated part from a second direction mutually opposite to the first direction using a second and third reflector, wherein, each of the reflectors irradiates the irradiated parts with exciting light in such a manner that the exciting light passes through the irradiated parts of all the capillaries included in a respective capillary array; and detecting light emission generated by the capillaries in the two capillary arrays by one optical detection system arranged in a direction perpendicular to the plane where the irradiated parts of the capillaries of the two capillary arrays are arranged, wherein:

the optical detection system simultaneously detects light emission generated by all of the capillaries used for measurement, the irradiated parts of the two capillary arrays are mounted at locations positioned across an optical transmission central axis of the optical detection system, as viewed from above, such that one irradiated part is positioned on one side of the central axis and another irradiated part is positioned on the other side of the central axis, the light cutoff means prevents transmitted light that has traveled through one of the capillary arrays from entering the other of the capillary arrays, in simultaneously detecting light emission at the optical detection system, both of the capillary arrays are in a state where they are fixed to the capillary electrophoresis apparatus, and signal intensities of all of the capillaries used for measurement vary by 0.13 or less.

6. The capillary electrophoresis apparatus according to claim 1, wherein the signal intensities of all of the capillaries used for measurement vary by 0.1 or less.

7. A capillary electrophoresis apparatus, comprising:
a single exciting light source;
two capillary arrays, each consisting of a plurality of capillaries having irradiated parts adapted to be irradiated with exciting light and arranged in parallel on a plane in such a way that the irradiated parts of the capillaries contained in each array are arranged in parallel with each other on the same plane;
a beam splitter configured to split light from the single exciting light source;
a first reflector configured to lead a first light from the beam splitter in a first direction to a first irradiated part, and second and third reflectors configured to lead a second light from the beam splitter to a second irradiated part from a second direction mutually opposite to the first direction, therein, each of the reflectors is adapted to irradiate the irradiated parts with exciting light such a manner that the exciting light passes through the irradiated parts of all the capillaries included in a respective capillary array;
light cutoff means arranged between the irradiated parts of the capillaries of the two capillary arrays, wherein the light cutoff means is configured to prevent light from entering an adjacent capillary array;
and
one optical detection system arranged in a direction perpendicular to the plane where the irradiated parts of the capillaries contained in the two capillary arrays are arranged, the optical detection system being adapted to detect light emission generated by the capillaries contained in the two capillary arrays, wherein:
each of the capillary arrays is individually removable,
the optical detection system simultaneously detects light emission generated by all of the capillaries used for measurement,
the irradiated parts of the two capillary arrays are positioned across an optical transmission central axis of the optical detection system, as viewed from above, such that one irradiated part is positioned on one side of the central axis and another irradiated part is positioned on the other side of the central axis,
the light cutoff means prevents transmitted light that has traveled through one of the capillary arrays from entering the other of the capillary arrays,
in simultaneously detecting light emission at the optical detection system, both of the capillary arrays are in a state where they are fixed to the capillary electrophoresis apparatus, and
signal intensities of all of the capillaries used for measurement vary by approximately 0.13.

8. The capillary electrophoresis apparatus according to claim 3, wherein the signal intensities of all of the capillaries used for measurement vary by 0.1 or less.

9. A capillary electrophoresis apparatus from which two capillary arrays, each consisting of a plurality of capillaries having irradiated parts adapted to be irradiated with exciting light and arranged in parallel on a plane, can independently be removed in such a way that the irradiated parts of the capillaries contained in each array are arranged in parallel with each other on the same plane, comprising:
a single exciting light source;
a mounting surface on which the irradiated parts of the capillaries of the two capillary arrays are mounted so as to be arranged in parallel with each other and on the same plane;
a beam splitter configured to split light from the single exciting light source;
a first reflector configured to lead a first light from the beam splitter in a first direction to a first irradiated part, and second and third reflectors configured to lead a second light from the beam splitter to a second irradiated part from a second direction mutually opposite to the first direction, wherein, each of the reflectors is adapted to irradiate the irradiated parts with exciting light in such a manner that the exciting light passes through the irradiated parts of all the capillaries included in a respective capillary array;
light cutoff means arranged between mounting positions of the irradiated parts of the capillaries of the two capillary arrays on the mounting surface, wherein the light cutoff means is configured to prevent light from entering an adjacent capillary array;
and
one optical detection system arranged in a direction perpendicular to the mounting surface of the two capillary arrays, the optical detection system being adapted to simultaneously detect light emission generated by the capillaries in the two capillary arrays mounted on the capillary electrophoresis apparatus, wherein:
each of the capillary arrays is individually removable,
the optical detection system simultaneously detects light emission generated by all of the capillaries used for measurement, the irradiated parts of the two capillary arrays are mounted at locations positioned across an optical transmission central axis of the optical detection system, as viewed from above, such that one irradiated part is positioned on one side of the central axis and another irradiated part is positioned on the other side of the central axis, the light cutoff means prevents transmitted light that has traveled through one of the capillary arrays from entering the other of the capillary arrays, in simultaneously detecting light emission at the optical detection system, both of the capillary arrays are in a state where they are fixed to the capillary electrophoresis apparatus, and signal intensities of all of the capillaries used for measurement vary by approximately 0.13.

* * * * *